(12) United States Patent
Kojima et al.

(10) Patent No.: US 6,200,540 B1
(45) Date of Patent: Mar. 13, 2001

(54) UREA SYNTHESIS APPARATUS

(75) Inventors: Yasuhiko Kojima; Hidetsugu Fujii, both of Chiba (JP)

(73) Assignee: Toyo Engineering Corporation, Tokyo (JP)

( * ) Notice: Subject to any disclaimer, the term of this patent is extended or adjusted under 35 U.S.C. 154(b) by 0 days.

(21) Appl. No.: 09/307,807

(22) Filed: May 10, 1999

Related U.S. Application Data

(62) Division of application No. 08/939,126, filed on Sep. 26, 1997, now Pat. No. 5,936,122.

(30) Foreign Application Priority Data

Oct. 7, 1996 (JP) .................................................. 8-265969
Oct. 22, 1996 (JP) .................................................. 8-279472
Aug. 29, 1997 (JP) .................................................. 9-234364

(51) Int. Cl.⁷ .................................................... B01J 10/00
(52) U.S. Cl. ............................ 422/189; 422/193; 422/194
(58) Field of Search ................................. 422/189, 188, 422/193, 194, 195; 159/47.2; 564/67, 68, 70, 71, 72

(56) References Cited

U.S. PATENT DOCUMENTS

| 3,406,201 | 10/1968 | Baumann et al. . |
| 3,867,442 | 2/1975 | Logemann . |
| 4,208,347 | 6/1980 | Pagani . |
| 5,750,780 | * 5/1998 | Rescalli .................................. 564/67 |

FOREIGN PATENT DOCUMENTS 0 329 215  8/1989  (EP) .
0 155 735  9/1995  (EP) .

\* cited by examiner

*Primary Examiner*—Shrive Beck
*Assistant Examiner*—Susan Ohorodnik
(74) *Attorney, Agent, or Firm*—Oblon, Spivak, McClelland, Maier & Neustadt, P.C.

(57) ABSTRACT

A vertical condenser is installed on or above a urea synthesis column to condense the mixed gas from the stripper by bringing it into contact with an absorption medium under cooling. A first down pipe for making the top part of the condenser communicate with the bottom part of the synthesis column is provided to allow the resultant condensate to flow down to the bottom part of the synthesis column by gravity. The condensate is subjected to urea synthesis together with feed ammonia or a part of feed carbon dioxide supplied thereto. The urea synthesis solution thus formed is introduced into the stripper by gravity through a second down pipe having an opening in the top part of the synthesis column. Unreacted ammonia and carbon dioxide are separated as the aforesaid mixed gas by the rest of the feed carbon dioxide and introduced into the bottom part of the aforesaid condenser so as to be condensed. Alternatively, the condensate from the vertical condenser is sucked by means of an ejector using preheated feed liquid ammonia as the driving fluid, so that it is introduced into the bottom part of the urea synthesis column and is subjected to urea synthesis.

6 Claims, 4 Drawing Sheets

UREA SYNTHESIS APPARATUS

This is a division of application Ser. No. 08/939,126 filed Sep. 26, 1997, now U.S. Pat. No. 5,936,122 granted Aug. 10, 1999.

BACKGROUND OF THE INVENTION

1. Field of the Invention

The invention relates to an improved urea synthesis process comprising separating unreacted ammonia and carbon dioxide under a pressure nearly equal to the urea synthesis pressure by means of carbon dioxide stripping, wherein the synthesis column and the like can be placed on the ground.

2. Description of the Related Art

It is well-known to produce urea by processes which comprise reacting ammonia with carbon dioxide in a urea synthesis zone under a pressure and temperature of urea synthesis, separating unreacted ammonium carbamate as a mixed gas of ammonia and carbon dioxide from the resultant urea synthesis solution, absorbing the mixed gas by an absorption medium to recycle the resulting absorbate to the urea synthesis zone, and providing a urea solution from the urea synthesis solution from which the ammonium carbamate has been separated. A variety of proposals have been made regarding the urea synthesis process of this type.

Though depending on the process it employs and its production scale, the urea plant comprises a synthesis column, a carbamate condenser and a stripper, of which the synthesis column and the carbamate condenser have sometimes been placed at a height of 20–30 m from the ground level on their bottom basis. Where these equipments are placed at a height of 20–30 m from the ground level, structures supporting these equipments only by structural members such as steel frames have never been employed and concrete and the like functioning as the foundation have been constructed upto this height or a combination thereof with steel-framed structural members has been employed. In view of this background, there have been developed urea synthesis processes in which the urea synthesis column and the like are placed on the ground, by reason that it takes much time and labor to install and maintain these equipments at the height, or by the like reasons.

As an example of the processes suggesting the ground placement, an improved urea synthesis process disclosed in Japanese Patent Laid-Open Publication No. 149930/1978 is mentioned. According to this process, in an equal pressure double-flow recycle process for synthesizing urea with intermediate ammonium carbamate, which comprises reacting ammonia with carbon dioxide at a high ammonia to carbon dioxide molar ratio (hereinafter simply referred to as N/C), heat-treating the synthesis product in the presence of a stripping agent under substantially the same pressure as that of the synthesis, and recycling the remaining materials and the excess material separated from the synthesis product in two separate streams under the same pressure, (1) the urea synthesis product is treated in two continuous steps under the same pressure as that of the urea synthesis, and in the first step, the above-mentioned product is heated to decompose substantially all of the remaining ammonium carbamate and the decomposition product is discharged together with part of the excess ammonia, while in the second step, the remaining part of the excess ammonia is discharged by the addition of supplementary heat and the introduction of a carbon dioxide stream, and (2) the gaseous phase stripped off in the first step is recycled directly to the synthesis, and the gaseous phase stripped off in the second step is subjected to condensation and a residual gas purge treatment and then recycled to the synthesis in a liquid state.

The synthesis pressure used therein is 100–250 kg/cm$^2$, preferably 180–225 kg/cm$^2$, and the synthesis temperature is 170–205° C., preferably 180–200° C.

The synthesis part comprises two separate synthesis autoclaves continuously arranged in two steps or it is comparted into two steps by completely dividing a synthesis autoclave into the upper and lower sections by means of a partition plate provided in the lower part of the autoclave. As synthesis conditions in the synthesis autoclave located above (hereinafter referred to as the first zone) and the synthesis autoclave located below (hereinafter referred to as the second zone), the N/C in the second zone should always be larger than the NIC in the first zone. The N/C is 4–7 in the first zone, while it is 6–8 in the second zone. Separately, strippers are provided in a number of two, and the excess amount of ammonia dissolved in the liquid phase is recovered in the first step of the two stripping steps and introduced into the first zone, while the gaseous phase stripped off in the second step of the stripping steps is subjected to condensation and a residual gas purge treatment, and thereafter the condensate is recycled to the first zone.

As an attendant effect of this process, it is described in the upper left column on page 6 in the aforementioned publication that by using a reactor having both the upper and lower sections, it is possible to avoid the installation of a gigantic and unmanageable scaffold that is usually necessary for installing a reactor at a height. This suggests that the autoclave is of a self-supporting type.

Among other examples of the process suggesting the ground placement is EP-0329215A1. This patent publication discloses a process in which a carbamate condenser is installed at a high ground and a part of the stripper gas is introduced into the synthesis section by means of an ejector, suggesting that the synthesis column, stripper and the like can be installed directly on the ground.

Although the above-mentioned two conventional techniques suggest the installation of the synthesis column, stripper and the like directly on the ground, they need to place the carbamate condenser at a height and sometimes to use an ejector.

Then, an illustration is made on a urea production process disclosed in Japanese Patent Laid-Open Publication No. 209555/1985. Unlike the above-mentioned two conventional techniques, this process permits the achievement of a high urea synthesis rate and the recovery of the heat of condensation of a gaseous mixture from the stripping treatment by a small heat-exchanging area. In this process, in the production of urea comprising forming a urea synthesis solution comprising ammonium carbamate and free ammonia (excess ammonia) from carbon dioxide and ammonia in excess in a synthesis zone under a pressure of 125–350 bar, decomposing at least a part of the ammonium carbamate present in the urea synthesis solution by the addition of heat and a counter-current contact with a stripping gas in a stripping zone under a pressure not higher than the pressure in the synthesis zone, removing the decomposition product of ammonium carbamate from the stripping zone as a gas mixture together with a part of the excess ammonia and the stripping gas, condensing at least a part of the resultant gas mixture in a condensation zone, and treating the urea synthesis solution having undergone the stripping to obtain a urea solution or solid urea, at least 30% of the equilibrium amount of urea attainable under the reaction conditions is formed even in the condensation zone, and the mixture containing ammonium carbamate and urea is supplied to the synthesis zone. The condensation in the condensation zone is carried out under the synthesis pressure or the pressure of the stripping treatment lower than the synthesis pressure. Further, the condensation is effected in a submerged condenser, particularly in the shellside of a shell and tube heat exchanger arranged horizontally. The condensation can also be practiced in a condensation zone integrated with the reaction zone.

In the upper left column on page 4 of the publication, however, it is mentioned that the dip-type condenser may be arranged horizontally or vertically and it is particularly preferable to carry out the condensation in a vertical submerged condenser. It is also described that where a horizontal condensation zone is applied, a synthesis zone and the condensation zone can be accommodated within an equipment so that a compact structure is obtained. However, it only suggests an example of the application of a vertical condensation zone, that is, the accommodation of the synthesis zone and the condensation zone within an equipment.

Further, there is also a description that where a horizontally arranged submerged condenser is used, it can be disposed directly on the working floor, thus lowering the height of the equipment, reducing the cost of the equipment, and facilitating its assembly and dismantlement. This description however does not teach the ground placement of the equipments.

SUMMARY OF THE INVENTION

It is an object of the present invention to provide an improved process capable of placing the equipments on the ground in a urea synthesis process comprising a step of stripping unreacted ammonia and carbon dioxide by feed carbon dioxide under a pressure substantially equivalent to the urea synthesis pressure and a step of condensing the mixed gas from the stripping step.

The present invention provides a urea synthesis process as described below and an apparatus therefor.

An aspect of the present invention is as follows:

In a urea synthesis process comprising reacting ammonia with carbon dioxide at a urea synthesis temperature and pressure in a urea synthesis zone, bringing the resultant urea synthesis solution containing urea, unreacted ammonia, unreacted carbon dioxide and water into contact with at least a part of feed carbon dioxide under heating under a pressure nearly equal to said urea synthesis pressure in a stripping zone to separate said unreacted ammonia and said unreacted carbon dioxide as a mixed gas of ammonia, carbon dioxide and water, treating further the urea synthesis solution containing unseparated unreacted ammonia and unreacted carbon dioxide to obtain urea, introducing the mixed gas separated in said stripping zone into the bottom part of a vertical condensation zone to bring it into contact with an absorption medium under cooling thereby to condense said mixed gas, and recycling the thus-obtained condensate to the urea synthesis zone, the improvement which comprises installing the urea synthesis zone in a lower part and the vertical condensation zone thereon or thereabove, providing a first down pipe that has an opening in each of the top part of said condensation zone and the bottom part of said urea synthesis zone and is for making said condensation zone communicate with said urea synthesis zone, letting said condensate flow down to the bottom part of said urea synthesis zone by gravity through said down pipe from the top part of said condensation zone, subjecting the condensate having flowed down to the urea synthesis reaction while it goes up through said urea synthesis zone, and letting the thus-formed urea synthesis solution flow down to the top part of said stripping zone through a second down pipe having an opening in the top part of said urea synthesis zone.

Another aspect of the present invention is as follows:

A urea synthesis apparatus which comprises (a) a vertical urea synthesis column, (b) a vertical condenser with a cooler, installed on or above said urea synthesis column, (c) a stripper for stripping unreacted ammonia and unreacted carbon dioxide, contained in a urea synthesis solution from said urea synthesis column, by means of feed carbon dioxide to separate them from the solution as a mixed gas of ammonia, carbon dioxide and water, (d) a first down pipe that has an opening in each of the top part of said condenser and the bottom part of said urea synthesis column and is for making said condenser communicate with said urea synthesis column to allow the condensate to flow down from the top part of said condenser to the bottom part of said urea synthesis column by gravity, (e) a piping for introducing feed ammonia or feed carbon dioxide into the bottom part of said urea synthesis column, (f) a second down pipe that has an opening in the top part of said urea synthesis column and is for introducing the urea synthesis solution into the top part of said stripper by gravity, (g) a piping for introducing said mixed gas from said stripper into the bottom part of said condenser, (h) a piping for introducing an absorption medium or an absorption medium and feed ammonia into the bottom part of said condenser, (i) a piping for discharging inert gas, joined to the top part of said condenser, (j) a piping for introducing at least a part of feed carbon dioxide, joined to the bottom part of said stripper, and (k) a piping for discharging the aqueous urea solution containing unseparated unreacted ammonia and unreacted carbon dioxide from the bottom part of said stripper for further treatments.

A further aspect of the present invention is as follows:

In a urea synthesis process which comprises reacting ammonia with carbon dioxide at a urea synthesis temperature and pressure in a urea synthesis zone, bringing the resultant urea synthesis solution containing urea, unreacted ammonia, unreacted carbon dioxide and water into contact with at least a part of feed carbon dioxide in a stripping zone under heating under a pressure nearly equal to said urea synthesis pressure to separate unreacted ammonia and unreacted carbon dioxide as a mixed gas of ammonia, carbon dioxide and water, treating further the urea synthesis solution containing unseparated unreacted ammonia and carbon dioxide to obtain urea, introducing the mixed gas separated in said stripping zone into the bottom part of a vertical condensation zone to bring it into contact with an absorption medium under cooling thereby to condense said mixed gas, and recycling the thus-obtained condensate to the urea synthesis zone, the improvement which comprises preheating feed liquid ammonia to supply it to an ejector under a pressure of 150–300 bar, expanding said liquid ammonia through the ejector so that the pressure difference between the delivery pressure and the suction pressure of the ejector may become 2–10 bar thereby to suck the condensate from the top part of said vertical condenser, introducing the mixture of said liquid ammonia and said condensate from said ejector into the bottom part of said urea synthesis zone, subjecting said introduced mixture to the urea synthesis while it goes up through said urea synthesis zone, and supplying the thus-formed urea synthesis solution from the top part of said urea synthesis zone to the top part of said stripping zone.

A further aspect of the present invention is as follows:

A urea synthesis apparatus comprises (a) a vertical urea synthesis column installed on the ground, (b) a vertical condenser with a cooler, installed on the ground, (c) a stripper for stripping unreacted ammonia and unreacted carbon dioxide, contained in a urea synthesis solution from said urea synthesis column, by means of feed carbon dioxide to separate them from the solution as a mixed gas of ammonia, carbon dioxide and water, (d) a heat-exchanger for preheating feed liquid ammonia, (e) an ejector for sucking the condensate from said condenser by using the preheated feed liquid ammonia as the driving fluid, (f) a down pipe that has an opening in the top part of said condenser and is for supplying said condensate to the ejector, (g) a piping for supplying said feed liquid ammonia to the ejector through the heat-exchanger, (h) a piping for supplying the mixture of the feed liquid ammonia and the condensate from the ejector to the bottom part of said urea synthesis column, (i) a piping for supplying the urea synthesis solution from said urea synthesis column to said stripper, (j) a piping for supplying feed carbon dioxide to said stripper, or to said stripper and said urea synthesis column, (k) a piping for supplying the mixed gas separated in said stripper to the bottom part of said condenser, (l) a piping for discharging the aqueous urea solution containing unseparated unreacted ammonia and unreacted carbon dioxide from the bottom part of said stripper for further treatments, and (m) a piping for supplying an absorption medium to the bottom part of said condenser.

A still further aspect of the present invention is as follows:

A urea synthesis apparatus which comprises (a) a vertical urea synthesis column, (b) a vertical condenser with a cooler, installed on or above said urea synthesis column, (c) a stripper for stripping unreacted ammonia and unreacted carbon dioxide, contained in a urea synthesis solution from said urea synthesis column, by means of feed carbon dioxide to separate them from the solution as a mixed gas of ammonia, carbon dioxide and water, (d) a heat-exchanger for preheating feed liquid ammonia, (e) an ejector using the preheated feed liquid ammonia as the driving fluid, (f) a first down pipe that has an opening in the top part of said condenser and is for feeding the condensate from the top part of said condenser to the suction side of the ejector, (g) a piping for introducing the feed liquid ammonia and said condensate from the delivery side of the ejector into the bottom part of said urea synthesis column, (h) a second down pipe that has an opening in the top part of said urea synthesis column and is for introducing the urea synthesis solution into the top part of said stripper, (i) a piping for introducing said mixed gas from said stripper into the bottom part of said condenser, (j) a piping for introducing an absorption medium or an absorption medium and feed ammonia into the bottom part of said condenser, (k) a piping for discharging inert gas, joined to the top part of said condenser, (l) a piping for introducing at least a part of feed carbon dioxide, joined to the bottom part of said stripper, and (m) a piping for discharging the aqueous urea solution containing unseparated unreacted ammonia and unreacted carbon dioxide from the bottom part of said stripper for further treatments.

DESCRIPTION OF THE PREFERRED EMBODIMENT

In the present invention, the urea synthesis rate based on carbon dioxide is the percentage of the molar amount of the carbon dioxide converted to urea relative to the molar amount of the total carbon dioxide, which is simply referred to as a urea synthesis rate hereunder. Further, the inert gas represents a general name of the air introduced into the urea synthesis column, stripper, condenser and the like to prevent corrosion and impurities originally involved in the feed carbon dioxide.

The vertical condenser is a heat-exchanger in which an ammonium carbamate condensate is caused to flow through the shellside, for example, a shell and tube heat-exchanger, which is vertically installed.

Figure 1:
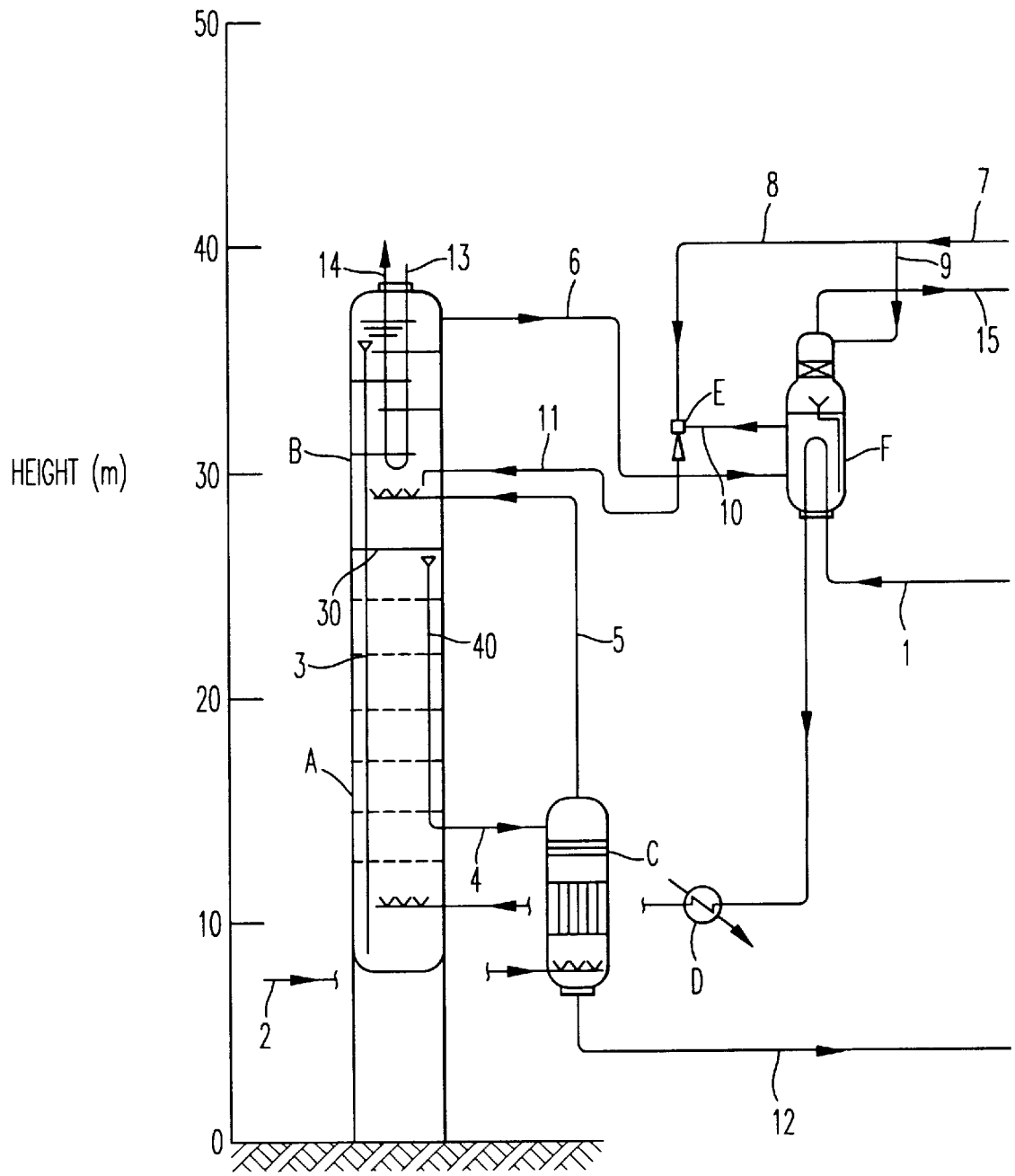
FIG. 1 is a flowsheet illustrating an embodiment of the present invention, indicating the height of each equipment from the ground level.
Figure 2:
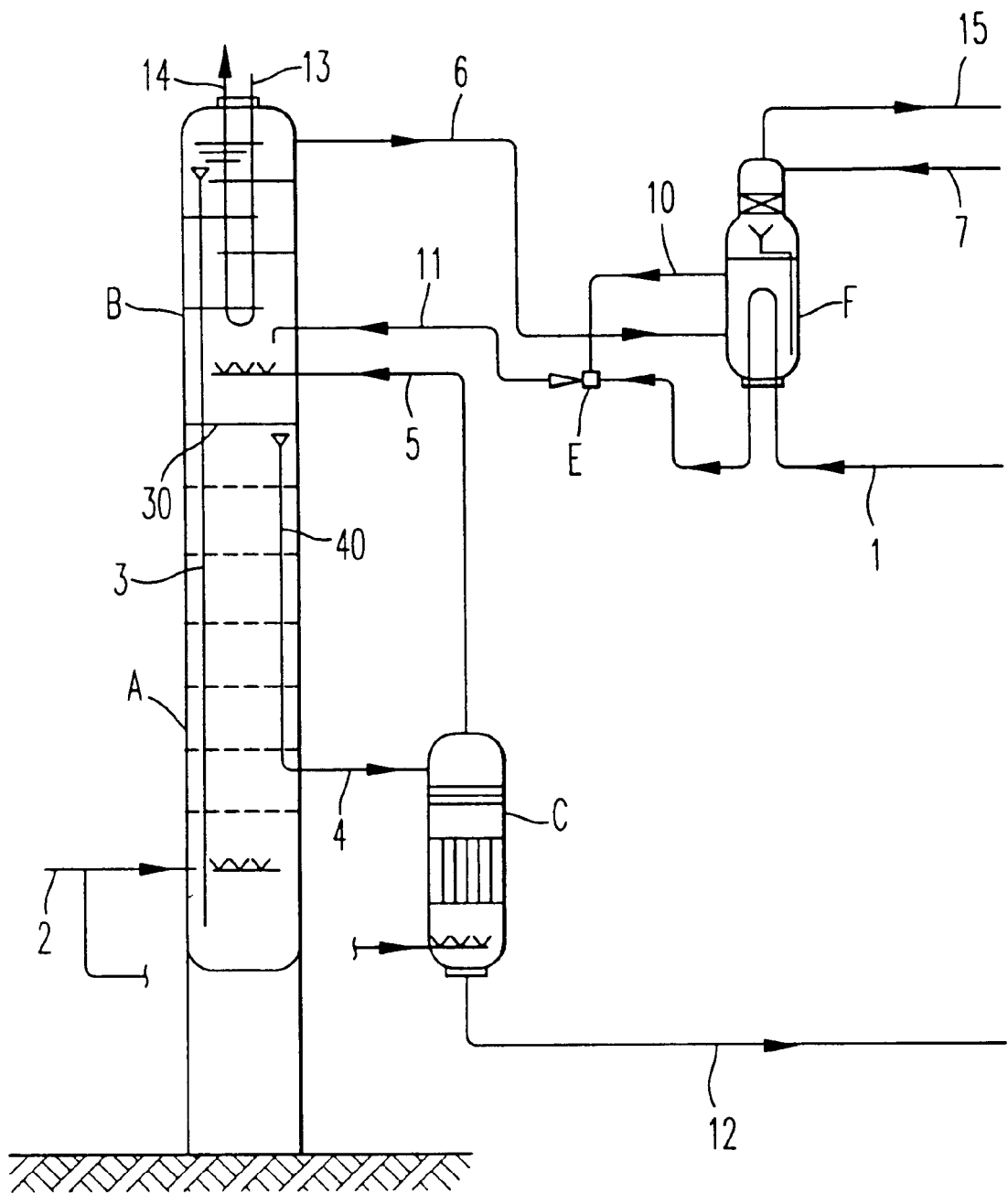
FIG. 2 is a flowsheet illustrating another embodiment of the present invention.

FIGS. 1 and 2 are flowsheets illustrating embodiments of the present invention, indicating the positions (heights from the ground level) at which the condenser, urea synthesis column, stripper and the like are installed. Although each of the equipments is described in detail later, it is explained in the following why each equipment can be placed on the ground in these embodiments.

Where a urea synthesis solution is allowed to fall down from a urea synthesis column A to a stripper C only by gravity, the solution does not flow in the absence of a head difference. Formerly, when the solution was allowed to flow from the bottom part of a synthesis column to the top part of a stripper, the positional difference between the synthesis column, particularly the bottom part of the synthesis column and the top part of the stripper, particularly the feeding part to the stripper, constituted the aforementioned head difference. Conventionally, in a process for producing 1,000–1,700 t/d of urea, 10–15 m have been employed as the aforesaid head difference. However, the head difference does not significantly vary even with the variation of production scale.

To attain the aforesaid head difference, a condenser B and a synthesis column A are integrated to provide a vertical condensation synthetic reaction apparatus of the integrated type, which has a first down pipe 3 for joining both the apparatuses directly to each other. The synthesis column employs such a structure that a second down pipe 40 provided below the vicinity of an internal partition plate 30 (made of the same material as the lining material of the synthesis column, e.g. improved 316LSS) is submerged in the synthesis column down to a position below an inlet provided in the top part of a stripper C, and connected from this position to the inlet provided in the top part of the stripper. By adopting this structure, the second down pipe can serve as a seal and secure a head difference of 10–15 m, so that it has become possible to place the equipment on the ground.

In the vertical condensation synthetic reaction apparatus, the position of the internal partition plate is selected to be 10–30 m from the ground level, though it depends more or less on the production scale of urea. For example, the plate is installed at about 27 m from the ground level in a plant producing 1,700 t/d of urea.

In the present invention, a vertical condenser is used. The reason is as follows. In a urea synthesis process to which the carbon dioxide stripping is applied, the feed to the condenser is an ammonium carbamate solution as the absorption medium and a mixed gas comprising carbon dioxide, that is the stripping gas sent from the stripper, excess ammonia, carbon dioxide and ammonia formed by decomposing ammonium carbamate, water, and inert gas. In the condenser, urea is not formed at a high urea synthesis rate unless the N/C is increased by causing the above-mentioned ammonium carbamate solution and the condensate formed in the condenser to absorb the aforesaid mixed gas fed to the condenser, though depending on the conditions including operating temperature and pressure. Further, it is necessary for the synthesis of urea to take a long residense time.

From the above viewpoint, the vertical condenser, in which the foregoing solution are caused to flow through the shellside, can secure a liquid depth necessary for the gas absorption, and can prolong the gas-liquid contact time by providing baffle plates, etc. because the aforementioned mixed gas is supplied to the vertical condenser at its bottom to form an upward-flowing gas-liquid concurrent flow in the shellside thereof, in addition to that it needs only a small area for its installation. Therefore, the residence time can be prolonged so that a larger amount of urea may be produced.

Further, by separating inert gas in the top part of the condenser, the proportion of the gas is greatly reduced in the synthesis column A described below, and therefore the urea synthesis reaction taking place essentially in the liquid phase becomes easy to proceed. Since corrosion preventive air, the aforesaid ammonium carbamate solution and the liquid condensed in the condenser are fully mixed in the condenser, dissolved oxygen necessary for preventing corrosion in the synthesis column is present in said mixed liquid, so that the synthesis column can be prevented from corrosion, even if the inert gas has been separated.

Down pipes are illustrated. A synthesis solution containing the urea formed in the condenser B at a urea synthesis rate of 20–60%, unreacted ammonia, unreacted carbon dioxide, and the like overflows into a first down pipe 3 and flows down therethrough by gravity into the synthesis column A.

Further, since the first down pipe is caused to reach the fully deep part in the lower section of the synthesis column, a liquid seal is formed so as to prevent the back flow of liquid and gas. As the material of the first down pipe, improved 316LSS is generally selected, which is the same material as that of the lining of the synthesis column.

The down pipe may also be a pipe running outside the equipment. A high pressure stainless steel pipe will suffice in this case.

A second down pipe 40, which has an opening below the vicinity of the partition plate 30, is arranged in the synthesis column A to provide a liquid seal effect. The urea synthesis solution flows through the second down pipe by gravity into the stripper.

Feed ammonia or feed carbon dioxide can be supplied to the synthesis column so as to attain a temperature of 180–200° C. in the column. When the feed material is supplied to the synthesis column, a density difference (hereinafter called a drafting force) occurs between the liquid having flowed down from the condenser to the synthesis column and the gas-liquid mixed fluid going up through the synthesis column. The drafting force is explained taking, as an example, the case of supplying feed ammonia through a line 1 to the synthesis column in FIG. 1. The feed liquid ammonia is prefeated in a heat-exchanger D and supplied to the synthesis column. At this moment, the N/C (3.5–4.5) in the synthesis column is maintained higher than the N/C (2.5–4.5) in the condenser, and the liquid density in the synthesis column is approximately 870 kg/m$^3$. The liquid density in the condenser is about 1,000 kg/m$^3$, and this difference of the densities constitutes the drafting force. The drafting force can further accelerate the flow by gravity and minimize the difference in height between the condenser and the stripper.

In the embodiments of FIGS. 1 and 2, the volume ratio of the condenser to the synthesis column is selected to be approximately 3:7–5:5, which is described specifically below. Though depending on the production rate of urea, if the volume of the condenser is less than 30% of the sum of the volumes of the synthesis column and the condenser, the residence time in the condenser is sometimes insufficient, while if it exceeds 50%, the residence time in the synthesis column is sometimes insufficient.

The relative positional relations of the condenser, urea synthesis column, and stripper in the embodiments of FIGS. 1 and 2 are generally illustrated such that when the ground-base height of the top of the condenser is assumed to be 100, the ground-base height of the bottom of the condenser is 50–80, the ground-base height of the top of the stripper being 20–50, the ground-base height of the bottom of the urea synthesis column being 5–30, the ground-base height of the bottom of the stripper being 3–10, and the difference in height between the bottom of the condenser and the top of the stripper is 10–60. With such relative positional relations, introduction of the condensate formed in the condenser B into the urea synthesis column A, introduction of the urea synthesis solution from the urea synthesis column A into the stripper C, and introduction of the mixed gas from the stripper C into the condenser B are carried out smoothly by gravity. Therefore, it is not necessary to use an ejector or to install the urea synthesis column at a high ground.

As shown in Example 1 and Reference Example 1 described below, if we assume the volume of the synthesis column of the conventional process, in which the reaction is carried out exclusively in the column, as 1, the sum of the volumes of the condenser and the synthesis column according to the present invention is less than 1, under the same urea synthesis conditions (at the same urea production rate), thus indicating reduction in the total volume.

Figure 3:
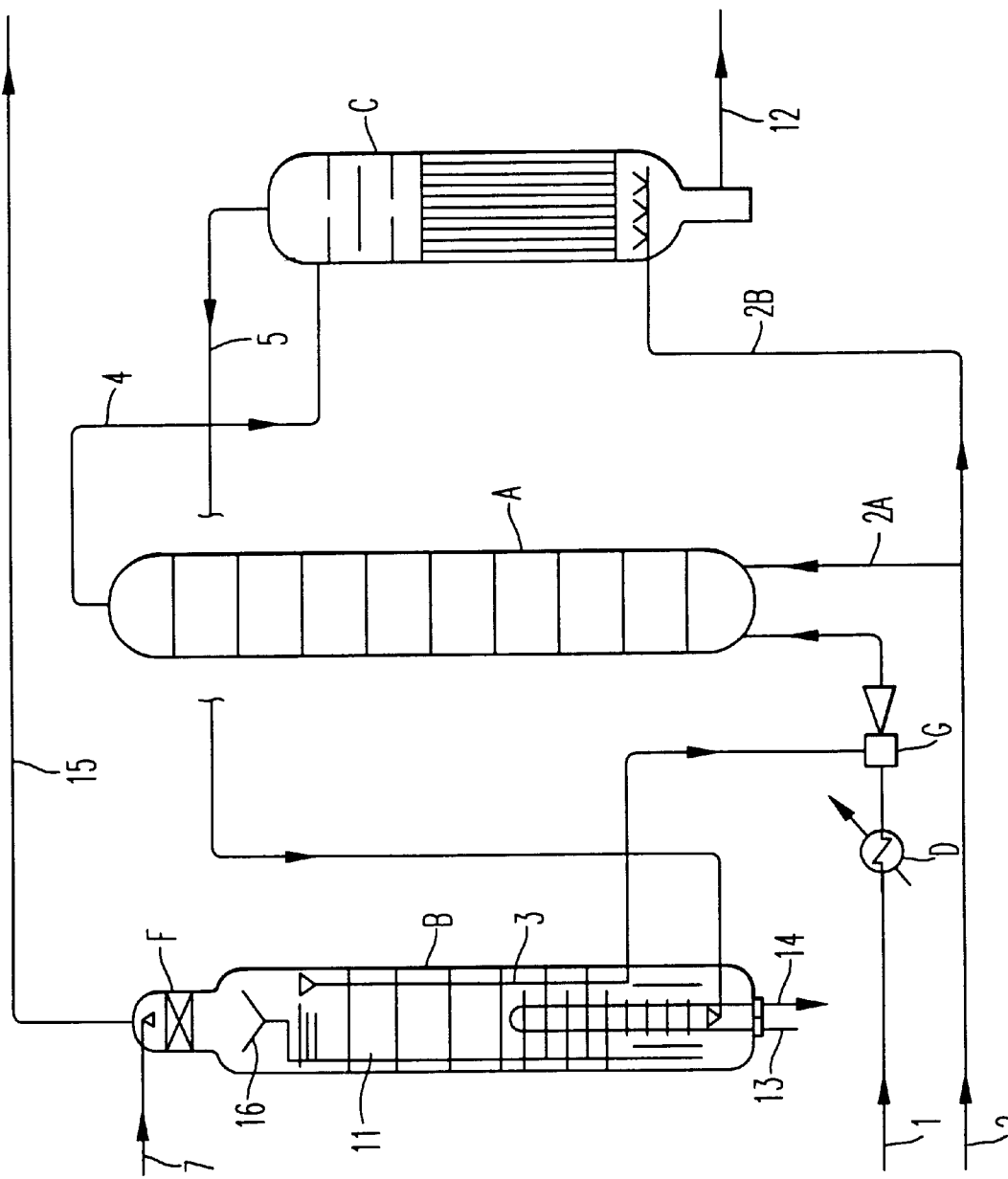
FIG. 3 is flowsheet illustrating a further embodiment of the present invention.
Figure 4:
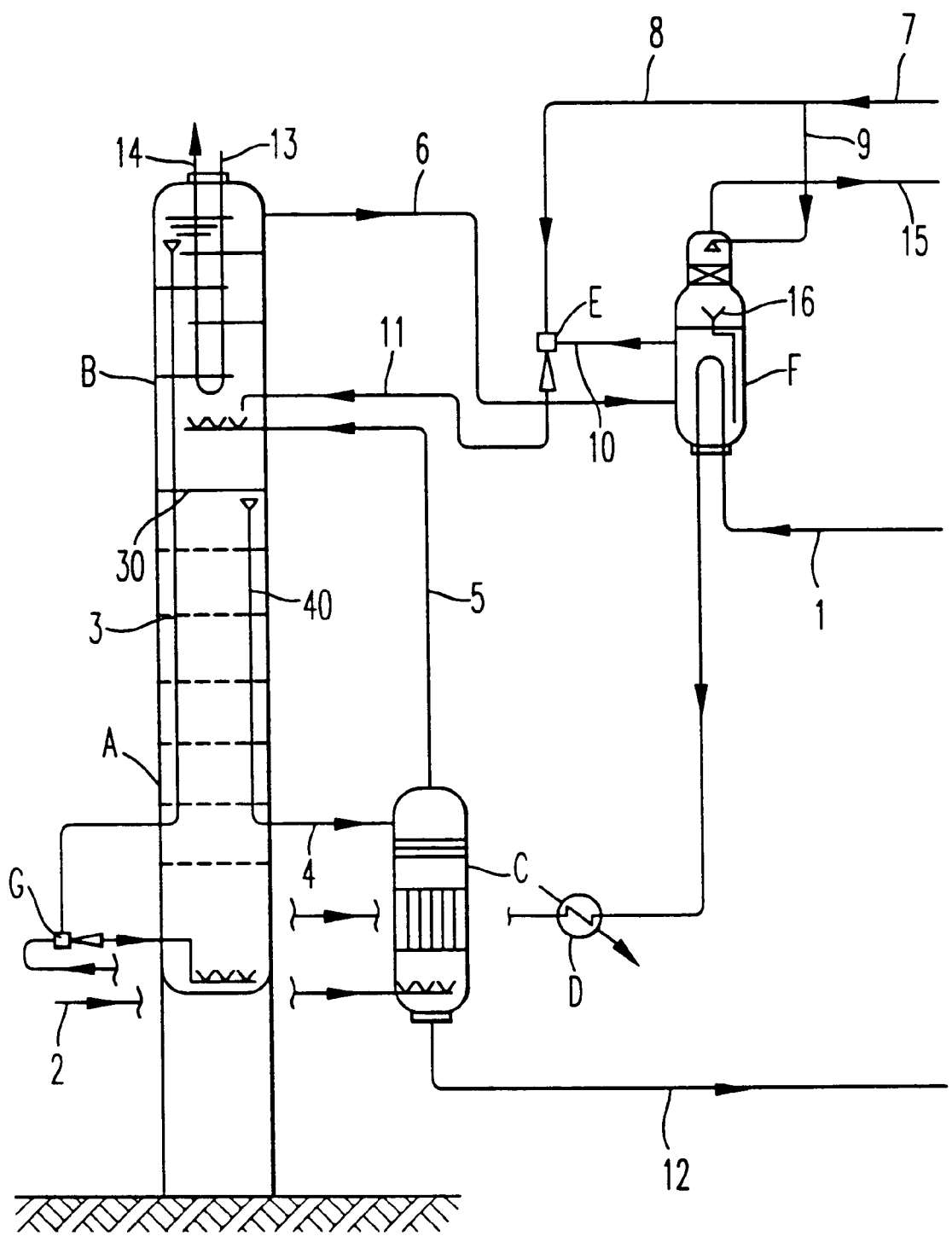
FIG. 4 is a flowsheet illustrating a still further embodiment of the present invention.

As mentioned above, since the synthesis column and the condenser are integrated and the condenser also has a urea synthesis function in the embodiments of FIGS. 1 and 2, the process of the present invention is clearly simplified and at the same time the integrated apparatus is made smaller in size, as compared with the conventional processes in which urea is synthesized exclusively in the synthesis column. Referring to FIGS. 1 and 2, the present invention is illustrated in detail in the case of recycling the liquids and gas to the condenser B, synthesis column A and stripper C only by head differences. In these drawings and FIGS. 3 and 4 shown later, common codes and numerals are used.

In FIGS. 1 and 2, a condenser B is installed on a urea synthesis column A and they are divided by a partition plate 30, a first down pipe 3 being so arranged as to make the top part of the condenser B communicate with the bottom part of the synthesis column A. Further, there is provided, in the synthesis column A, an independent second down pipe 40 having an opening below the vicinity of the partition plate 30 in order to provide a liquid seal effect.

FIGS. 1 and 2 shows an apparatus in which a condenser B and a urea synthesis column A are integrated through a partition plate dividing both the apparatuses. However, the condenser may be installed separately above the urea synthesis column, or the condenser and the urea synthesis column provided independently may be integrated by joining them together with the aid of, for example, a cylindrical body (which does not need pressure resistance).

The process of FIG. 1 is illustrated. A part of a recovery solution, which has been formed by recovering unreacted ammonia and carbon dioxide as an aqueous ammonium carbamate solution in a step not shown in the drawing, is introduced into a condenser B through lines 7, 8 and 11, while the rest is supplied to a scrubber F through a line 9. The recovery solution introduced into the vertical condenser B is brought into contact and mixed with a mixed gas comprising carbon dioxide, ammonia, inert gas, etc. fed to the condenser B through a line 5 from a stripper C described below, thereby absorbing the carbon dioxide and ammonia.

In the condenser B, the operating pressure is the same as the operating pressure of the synthesis column mentioned below, the N/C being 2.5–4.5, the H/C being 0.0–1.0, and the residence time is 10–30 minutes. The operating temperature is controlled at 170–190° C., and, under these conditions, a urea synthesis rate of 20–60% can be achieved.

When the N/C is less than 2.5, the condensation rate is decreased due to the increase of the partial pressure of carbon dioxide over the ammonium carbamate solution and the solidification temperature of ammonium carbamate is increased, while if the N/C exceeds 4.5, the condensation rate is also reduced due to the increase of the vapor pressure of ammonia. Therefore, it is preferable to avoid any of these N/Cs. Any H/C exceeding 1.0 reduces the equilibrium synthesis rate of urea and hence is preferably avoided. If the residence time is less than 10 minutes, the vapor pressures are increased and the condensation rate is decreased due to reduction in the urea synthesis rate. Further, even if it exceeds 30 minutes, the urea synthesis rate will not be improved so significantly in proportion to the length of time, and the volume of the condenser is uselessly and excessively increased. Therefore, any residence time outside the above range is preferably avoided. The operating temperature lower than 170° C. leads to reduction in the urea synthesis rate, while that in excess of 190° C. results in the reduction of the condensation rate due to the increase of the vapor pressures and in the corrosion of the material of the equipment. Accordingly, any of these operating temperatures is preferably avoided.

The foregoing recovery solution supplied to the scrubber F absorbs ammonia and carbon dioxide in the inert gas containing small amounts of ammonia and carbon dioxide introduced into the scrubber F through a line 6. The recovery solution corresponding to the increment produced by absorbing the ammonia and carbon dioxide is fed through a line 10 to an ejector E where it is pressurized and introduced into the condenser B through a line 11. Separately, the inert gas is discharged into the air from the scrubber F at the top.

In the drawing, an example of using an ejector E is illustrated. Needless to say, the present invention is not limited to this example. Where the ejector E is used, said recovery solution is divided in two between the scrubbe F and the ejector E, one being used for scrubbing the inert gas in the packed bed of the scrubber F, while the other is used to increase pressure through the ejector E at an outlet of the scrubber F. However, if the scrubber F is installed at a position above the condenser B, the ejector E is not necessary as a matter of course.

A part of feed carbon dioxide is supplied to a stripper C through a line 2. Although not described in the drawing, corrosion preventive air is also supplied to the stripper C. A synthesis solution comprising urea, ammonium carbamate, ammonia, etc. is fed through a second down pipe 40 in the synthesis column A to the stripper C, where it undergoes stripping under heating by means of the carbon dioxide. Its operating conditions are usually a pressure of 140–200 bar and a temperature of 160–200° C. The rest of the feed carbon dioxide is supplied, for example, to a low pressure decomposition column, which is not shown in the drawing. A urea synthesis solution comprising urea and unreacted ammonia and carbon dioxide is taken out of the stripper at its bottom and sent to the low pressure decomposition step through a line 12.

Feed liquid ammonia is preheated, for example, to 70–90° C., introduced through a line 1, further preheated through the scrubber F and a heat exchanger E, and supplied to the bottom part of the synthesis column A. In the synthesis column A, the liquid ammonia is joined with a synthesis solution having flowed down through a first down pipe 3 from the condenser B. The resultant solution moves up to the top part of the synthesis column and is supplied to the stripper C through a second down pipe 40 provided in the synthesis column and a line 4.

The operating pressure of the synthesis column is selected to be 130–250 bar as in the conventional processes. The N/C, the H/C, and the residence time are selected to be 3.5–5.0, 1.0 or less, and 10–40 minutes, respectively. The operating temperature is controlled at 180–200° C., and a urea synthesis rate of 60–75% is attained under the above conditions.

If the N/C is less than 3.5, the equilibrium synthesis rate is low, whereas if it exceeds 5.0, the vapor pressure of ammonia is increased due to its gasification. Therefore, any N/C outside the above range is preferably avoided. Any H/C exceeding 1.0 leads to reduction in the synthesis rate and therefore is preferably avoided. When the residence time is less than 10 minutes, the time is insufficient for the urea synthesis rate to achieve nearly its equilibrium value, while even when the time exceeds 40 minutes, the urea synthesis rate has already reached nearly its equilibrium value. Therefore, any residence time outside the above range is preferably avoided.

The process of FIG. 2 is now described. It is a substitution for the process shown in FIG. 1 in the following way. In FIG. 1, feed liquid ammonia is fed to the synthesis column, while feed carbon dioxide is fed to the condenser via the stripper. The process of FIG. 2 however differs in that feed liquid ammonia is fed to the condenser, and a part of feed carbon dioxide is supplied to the condenser through the stripper, the rest being fed to the synthesis section. In these drawings, basic large differences are in the operating conditions, particularly the N/Cs in the condenser and the synthesis column.

In the process of FIG. 2, the operating conditions of the condenser are an N/C of 3.0–4.5, an H/C of 1.0 or less, a temperature of 160–180° C., and a pressure equivalent to that of the synthesis column. The operating conditions of the synthesis column are such that the N/C is 3.0–4.0, the H/C being 1.0 or less, the temperature being 180–200° C., and the pressure is 130–250 bar.

Another embodiment of the present invention, namely a process in which an ejector is used for the introduction of the condensate into a synthesis column is illustrated specifically with reference to FIGS. 3 and 4. In the process of FIG. 3, feed liquid ammonia is introduced into a heat-exchanger D under a pressure of 150–300 bar, where it is preheated to 100–200° C., and enters an ejector G as the driving fluid.

The feed liquid ammonia is expanded through the ejector so that the pressure difference between the delivery and suction pressures of the ejector may become 2–10 bar. In consequence, the condensate supplied to the suction side of the ejector through a down pipe 3 in a vertical condenser B is sucked, pressurized, and introduced into the bottom part of a urea synthesis column A as a mixture with the driving fluid, the feed liquid ammonia. Of the feed carbon dioxide, carbon dioxide necessary for stripping unreacted ammonia and carbon dioxide is fed to the bottom part of a stripper C through lines 2 and 2b, and the rest is supplied to the bottom part of the urea synthesis column A through a line 2a or to a low pressure decomposition step not shown in the drawing.

The mixture of the feed liquid ammonia and the condensate from the ejector G and, if necessary, the carbon dioxide fed through a line 2a are reacted while going up through the urea synthesis column A to attain a total urea synthesis rate of 60–75%. In the urea synthesis column A, the pressure, the N/C, the H/C, and the residence time are preferably 130–250 bar, 3.5–5.0, 1.0 or less, and 10–40 minutes, respectively.

If the N/C is less than 3.5, the equilibrium synthesis rate is low, whereas if it exceeds 5.0, ammonia is gasified to increase its vapor pressure. Therefore, these N/Cs are preferably avoided. When the residence time is less than 10 minutes, the time is insufficient for the urea synthesis rate to attain nearly its equilibrium value, whereas even when it exceeds 40 minutes, the urea synthesis rate has already achieved nearly its equilibrium value, so that no more increase is expected in the synthesis rate. Therefore, these residence times are preferably avoided.

The urea synthesis solution comprising urea, unreacted ammonia, unreacted carbon dioxide and water formed in the synthesis column A are drawn out of the synthesis column at its top, and fed through a line 4 to the top part of the stripper C having a pressure substantially equal to or somewhat lower than the pressure in the synthesis column. The urea synthesis solution, while flowing down through the stripper C, is brought into contact, under heating, with feed carbon dioxide supplied to the bottom part of the stripper C through the line 2b to separate unreacted ammonia and carbon dioxide as a mixed gas of ammonia, carbon dioxide, inert gas and water. The mixed gas is introduced into the bottom part of the condenser B through a line 5 from the top of the stripper C. Air is also introduced into the stripper C to prevent corrosion of the equipments.

The operating conditions of the stripper are set at a pressure of 130–250 bar, particularly 140–200 bar, and a temperature of 160–200° C. The amount of feed carbon dioxide supplied to the stripper C and that of the carbon dioxide fed to the urea synthesis column A or the low pressure decomposition step are properly determined taking into consideration such conditions as the amounts of unreacted ammonia and carbon dioxide to be separated in the stripper C.

From the bottom part of the stripper C, an aqueous urea solution containing unseparated unreacted ammonia and unreacted carbon dioxide is taken out through a line 12 and sent to the low pressure treatment step where it is treated to produce urea.

A scrubber F is integrated on the top part of the condenser B. Needless to say, the scrubber F and the condenser B can be provided separately. A recovery solution from a low pressure recovery step (not shown) is supplied to the top part of the scrubber F through a line 7 as an absorption medium. The absorption medium is brought into contact with the inert gas from the condenser B to absorb the accompanying ammonia and carbon dioxide for their removal. The inert gas is discharged through a line 15.

Separately, the absorbed solution (the absorption medium having absorbed ammonia and carbon dioxide) from the scrubber F flows down to a receiver 16 provided in the bottom part of the scrubber F and then to the bottom part of the condenser B through a line (down pipe) 11 as an absorption medium for the mixed gas from the stripper. The absorption medium having flowed down is brought into contact with the mixed gas under cooling by a cooler shown by 13 and 14 to condense the gas. The condensate thus formed goes up through the condenser and is fed to the suction side of the ejector G through a down pipe 3 having an opening in the top part of the condenser. It is then sent to the bottom part of the synthesis column A together with the feed liquid ammonia as described above.

The operating pressure of the condenser B is nearly equal to that of the stripper C and is selected from 140–250 bar, and the temperature is controlled at 130–250° C., particularly 170–190° C. The N/C in the condenser B is 2.5–3.5, the H/C is 1.0 or less, and the residence time is 10–30 minutes. Under these conditions, a urea synthesis rate of 20–60% can be achieved.

In the condenser B, if the N/C is less than 2.5, the partial pressure of carbon dioxide over the condensate is increased, the condensation rate is reduced, and the solidification temperature of the condensate is increased, while if the N/C exceeds 3.5, the vapor pressure of ammonia is increased and hence the condensation rate is decreased. Therefore, any of these N/Cs is preferably avoided. Any H/Cs exceeding 1.0 reduce the equilibrium synthesis rate of urea and therefore are preferably avoided. When the residence time is less than 10 minutes, the vapor pressures are increased and the condensation rate is reduced due to the low rate of urea synthesis in the condenser, while even when it exceeds 30 minutes, a significant rise in the urea synthesis rate is not expected in the condenser in proportion to the prolonged length of time, which only increases the volume of the condenser. Any of these conditions is preferably avoided. Any operating temperature lower than 170° C. reduces the rate of urea synthesis, while any temperature above 190° C. leads to reduction in the condensation rate following increase in the vapor pressures and to the increase of the corrosion of the equipment. These operating temperatures are preferably avoided.

According to the process shown in FIG. 3, it is possible to place all of the synthesis column A, condenser B and stripper C on the ground. This is because even if the pressures of the condenser B and stripper C are selected to be somewhat lower than the pressure of the synthesis column and a pressure drop is placed between the stripper and the condenser to the extent that the mixed gas may flow from the stripper to the condenser, it becomes possible by the use of an ejector to introduce the condensate from the condenser to the synthesis column which is higher in pressure than the condenser.

Then, the process shown in FIG. 4 is illustrated. In this process, an apparatus is used, in which a vertical condenser B is arranged on a urea synthesis column A so that they may be integrated, as in the processes of FIGS. 1 and 2. Essentially, where such an equipment is used, the liquids and gas can be circulated through the urea synthesis column A, stripper C and condenser B by gravity even if the equipment is placed on the ground. However, since the condensate from the condenser is sucked, pressurized, and sent to the synthesis column A by means of an ejector G driven by feed liquid ammonia, the pressure distribution among the synthesis column A, stripper C and condenser B can be determined more freely.

In FIG. 4, a part of a recovery solution, which has been obtained by recovering unreacted ammonia and carbon dioxide as an aqueous ammonium carbamate solution in a step not shown in the drawing, is supplied as an absorption medium to the vertical condenser B through lines 7, 8 and 11, while the rest is fed to a scrubber F through a line 9.

The aforesaid recovery solution supplied to the vertical condenser B is brought into contact with a mixed gas comprising carbon dioxide, ammonia, inert gas and water fed from the stripper C through a line 5 to the condenser B to absorb the carbon dioxide and ammonia.

The operating pressure of the condenser is substantially the same as or somewhat lower than that of the synthesis column as described below and selected from 130–250 bar. The N/C, the H/C, and the residence time are selected from 2.5–3.5, 1.0 or below, and 10–30 minutes, respectively. The operating temperature is controlled at 130–250° C., particularly 170–90° C., and under the above conditions, an urea synthesis rate of 20–60% can be achieved in the condenser B.

In the condenser B, if the N/C is less than 2.5, the condensation rate is reduced due to increase in the partial pressure of carbon dioxide over the ammonium carbamate solution and the solidification temperature of ammonium carbamate is increased. On the other hand, if the N/C is higher than 3.5, the condensation rate is reduced due to increase in the vapor pressure of ammonia. Therefore, any of these N/Cs is preferably avoided. Any H/C in excess of 1.0 reduces the equilibrium synthesis rate of urea and hence is preferably avoided. When the residence time is less than 10 minutes, the vapor pressures are increased and the condensation rate is reduced because the urea synthesis rate is still low. Further, even when it exceeds 30 minutes, the urea synthesis rate is not expected to improve markedly in proportion to the length of time, and the volume of the condenser becomes excessively large. Therefore, any of these conditions is preferably avoided. Any operating temperature below 170° C. reduces the urea synthesis rate, while that in excess of 190° C. leads to reduction in the condensation rate following increase in the vapor pressures and to the corrosion of the material of the equipment. Therefore, these conditions are preferably avoided.

The recovery solution supplied to the scrubber F absorbs ammonia and carbon dioxide in the inert gas containing small amounts of ammonia and carbon dioxide introduced into the scrubber F through a line 6 and is recycled again to the scrubber F (not shown in the drawing). On the other hand, the inert gas is discharged into the air through a line 15 from the top of the scrubber F.

In FIG. 4, an example is illustrated in which an ejector E is used. However, the present invention is not limited to this example as a matter of course. In the case of using the ejector E, the above-mentioned recovery solution is divided in two between the scrubber F and the ejector E, and one is used for scrubbing the inert gas in the packed bed of the scrubber F, the rest being used for the pressure rise by the ejector E at the outlet of the scrubber F. Needless to say, where the scrubber F is placed at a position above the condenser B, the foregoing ejector E is unnecessary.

A part of feed carbon dioxide is supplied to the stripper C through a line 2. Though not described in the drawing, corrosion preventive air is also supplied to the stripper C. A synthesis solution comprising urea, ammonium carbamate, ammonia, etc. is supplied to the stripper C through a second down pipe 40 in the synthesis column A and a line 4, and undergoes stripping by carbon dioxide under heating. Regarding the operating conditions of the stripper C, commonly, the pressure is substantially the same as or somewhat lower than that of the synthesis column A and selected from 140–200 bar, while the temperature is selected from 160–200° C. The rest of the feed carbon dioxide is supplied, for instance, to a low pressure decomposition column, which is not described in the drawing. A solution containing urea and unseparated unreacted ammonia and carbon dioxide is withdrawn from the bottom of the stripper, and sent through a line 12 to the low pressure decomposition step where it is treated to obtain urea.

The feed liquid ammonia is preheated, for example, to 70–90° C., is imported through a line 1 to pass through a cooler of the scrubber F, further passes through a heat exchanger D at 150–300 bar to be preheated to 100–200° C., and is fed to an ejector G as the driving fluid. On the other hand, the condensate having flowed down by gravity through the first down pipe 3 from the top part of the condenser B is supplied to the suction side of the ejector G where it is pressurized and fed to the bottom part of the synthesis column A together with the driving fluid, the feed liquid ammonia, to undergo urea synthesis. The urea synthesis solution is supplied to the top part of the stripper C through the second down pipe 40 and the line 4 from the top part of the synthesis column A, as described above.

The operating pressure of the synthesis column A is selected to be 130–250 bar, as is the case with the conventional processes. Further, the N/C, the H/C, and the residence time are selected in the ranges of 3.5–5.0, 1.0 or less, and 10–40 minutes, respectively. The operating temperature is controlled at 180–200° C., and under the foregoing conditions, a total urea synthesis rate of 60–75% can be achieved.

In the synthesis column A, if the N/C is less than 3.5, the equilibrium synthesis rate is low, while if it exceeds 5.0, the gasification of ammonia is caused to increase the vapor pressure. Therefore, these conditions are preferably avoided. Any H/C in excess of 1.0 is preferably avoided because the urea synthesis rate is caused to decrease. When the residence time is less than 10 minutes, the time is insufficient for the urea synthesis rate to achieve nearly its equilibrium value, while even when it exceeds 40 minutes, the urea synthesis rate already has fully reached the vicinity of its equilibrium value. Therefore, these conditions are preferably avoided.

Further, all or a part of the rest of the feed carbon dioxide supplied to the stripper can be supplied to the synthesis column A so that the synthesis temperature may attain 180–200° C.

The apparatus formed by integrating a urea synthesis column and a condenser, used in the process shown in FIG. 4, is the same as that used in FIG. 1, except that an ejector is equipped.

The present invention is further illustrated in detail with reference to examples. However, it is needless to say that the present invention is not limited only to the examples described below.

EXAMPLE 1

Urea synthesis was carried out by an improved urea synthesis process, in which an apparatus with a daily production of 1,400 tons of urea placed on the ground was used as shown in FIG. 1.

791 t/d of feed ammonia and 1,025 t/d of feed carbon dioxide were supplied through a line 1 and a line 2, respectively. The feed ammonia heated to 175° C. by a steam condensate in a heat-exchanger D was fed to the bottom part of a synthesis column A through the line 1, while 969 t/d of the feed carbon dioxide and about 17 t/d of corrosion preventive air were fed to the bottom part of a stripper C through the line 2, the rest of the feed carbon dioxide being supplied to a low pressure decomposition column not illustrated in the drawing. Separately, 1314 t/d of a recovery solution as an absorption medium through a line 7, having a composition described below and a temperature of 108° C., were pressurized to 190 bar and divided in two between a scrubber F and an ejector E.

| urea | 0.4% |
|---|---|
| ammonia | 34.8% |
| carbon dioxide | 40.0% |
| water | 24.4% |

The recovery solution supplied to the scrubber F was used for scrubbing inert gas in the packed bed, while that supplied to the ejector E was used for pressurizing a scrubber delivery solution (line 10) by means of the ejector E. The scrubber F was operated at 175 bar and 175° C. The scrubber delivery solution (line 10) and the ejector-driving recovery solution (line 8) were mixed together by the ejector E and sent to the bottom part of a condenser B through a line 11.

A mixed gas comprising ammonia, carbon dioxide and water separated in the stripper C was sent to the bottom part of the condenser B through a line 5. The shellside of the condenser B was filled with the above-mentioned recovery solution and ammonium carbamate formed by condensation, by which the foregoing mixed gas was absorbed. The heat of absorption was removed by a cooler shown by lines 13 and 14. The condensate having absorbed the mixed gas stayed in the condenser for 15 minutes and flowed down through a first down pipe 3 by gravity to be fed to the synthesis column A. In the top part of the condenser, inert gas was withdrawn through a line 6.

The condensate from the condenser B which had been supplied to the bottom part of the synthesis column A was mixed with the above-mentioned liquid ammonia heated to 175° C. from the line 1, and while the mixture went up slowly through the synthesis column, the urea synthesis reaction further proceeded. The residence time for the reaction was 25 minutes. In the interior of the urea synthesis column A, baffle plates were arranged to accelerate the dispersion of gas and prevent the back mixing of liquid.

The synthesis solution sent to the stripper C through a second down pipe 40 and a line 4 from the synthesis column A was heated there so that the ammonium carbamate was decomposed and separated as a mixed gas of ammonia and carbon dioxide. The stripper C was operated at a top temperature of 191° C., a bottom temperature of 179° C., and a pressure of 175 bar.

As described above, the apparatus was operated by circulating the gas and liquids through the condenser B, urea synthesis column A and stripper C. The operating conditions and the compositions in the condenser B, synthesis column A, and stripper C are mentioned in Table 1. Reference Example 1 (corresponding to the process in FIG. 1):

In a conventional urea synthesis process (the condenser is not placed on the synthesis column, but the condenser and the synthesis column are installed at positions of 30 m and 28 m from the ground level, respectively), operation was practiced under the same operating conditions as in Example 1. The volume of the synthesis column in this case being taken as 1, it was compared with the total volume of the condenser and the synthesis column in Example 1. The results are also shown in Table 1.

EXAMPLE 2

A urea synthesis process illustrated in FIG. 2 was put in operation under the operating conditions of the condenser B, synthesis column A and stripper C as described in Table 1.

TABLE 1

|  | Example 1 | Example 2 | Ref. Ex. 1 |
|---|---|---|---|
| Feed ammonia (t/d) | 792 | 792 | — |
| Feed carbon dioxide (t/d) | 1025 | 1025 | — |
| Recovery solution (t/d) | 1314 | 1462 | — |
| Urea (%) | 0.4 | 0.4 | — |
| Ammonia (%) | 34.8 | 38.7 | — |
| Carbon dioxide (%) | 40.4 | 36.4 | — |
| Water (%) | 24.4 | 24.5 | — |
| Condenser B |  |  |  |
| Pressure (bar) | 175 | 170 | — |
| Temperature (° C.) | 185 | 170 | — |
| Urea (%) | 21.1 | 15.9 | — |
| Ammonia (%) | 34.3 | 47.5 | — |
| Carbon dioxide (%) | 26.7 | 21.6 | — |
| Water (%) | 17.9 | 15.0 | — |
| Urea synthesis rate (%) | 42.6 | 35.1 | — |
| N/C | 2.85 | 4.40 | — |
| H/C | 0.67 | 0.76 | — |
| Residence time (minutes) | 15 | 20 | — |
| Volume ratio | 0.34 | — | — |
| Synthesis column A |  |  |  |
| Pressure (bar) | 175 | 170 | 175 |
| Temperature (° C.) | 185 | 185 | 185 |
| Urea (%) | 31.8 | 32.4 | 31.8 |
| Ammonia (%) | 36.8 | 34.8 | 36.8 |
| Carbon dioxide (%) | 12.2 | 13.4 | 12.2 |
| Water (%) | 19.2 | 19.4 | 19.2 |
| Urea synthesis rate (%) | 65.7 | 63.9 | 65.7 |
| N/C | 4.0 | 3.70 | 4.0 |
| H/C | 0.67 | 0.64 | 0.67 |
| Residence time (minutes) | 25 | 30 | — |
| Volume ratio | 0.54 | — | 1.0 |
| Stripper C (line 12) |  |  |  |
| Urea (%) | 48.1 | 46.3 | — |
| Ammonia (%) | 13.2 | 15.5 | — |
| Carbon dioxide (%) | 13.7 | 13.5 | — |
| Water (%) | 25.0 | 24.7 | — |
| Stripper C (line 2) |  |  |  |
| Carbon dioxide (t/d) | 969 | 700 | — |

EXAMPLE 3

Urea synthesis was carried out by an improved urea synthesis process which employs an apparatus with a daily production of 1,400 tons placed on the ground as shown in FIG. 3.

792 t/d of feed ammonia and 1025 t/d of feed carbon dioxide were supplied through a line 1 and a line 2, respectively. The feed liquid ammonia with a pressure of 250 bar, which was introduced through the line 1 and heated to 175° C. by steam condensate in a heat exchanger D, was fed to the bottom part of a urea synthesis column A through an ejector G. Further, 969 t/d of the feed carbon dioxide and about 17 t/d of corrosion preventive air were respectively supplied to the bottom part of a stripper C through lines 2 and 2b, the rest of the feed carbon dioxide being supplied to a low pressure decomposition column not shown in the drawing (the amount of the feed carbon dioxide through a line 2a was assumed to be 0). Separately, 1314 t/d of a recovery solution fed through a line 7 as an absorption medium had the following composition and a temperature of 108° C. and was pressurized to 190 bar to be sent to a scrubber F.

| | |
|---|---|
| Urea | 0.4% |
| Ammonia | 34.8% |
| Carbon dioxide | 40.0% |
| Water | 24.4% |

The scrubber F was operated at 175 bar and 175° C. The delivery solution of the scrubber was supplied to the bottom part of the condenser B through a receiver 16 and a down pipe 11. Separately, inert gas was discharged through a line 15 from the scrubber F at its top.

A mixed gas comprising ammonia, carbon dioxide, water and inert gas, separated in the stripper C, was sent to the bottom part of the condenser B through a line 5. The shellside of the condenser B was filled with the foregoing recovery solution and ammonium carbamate formed by condensation, and the foregoing mixed gas was absorbed by the solution. The heat of absorption was removed in a cooler indicated by lines 13 and 14. The condensate having absorbed the mixed gas stayed in the condenser for 15 minutes, flowed down through a down pipe 3 by gravity, was pressurized by an ejector G, and then was sent to the bottom part of the synthesis column A.

The feed liquid ammonia and the condensate fed to the bottom part of the synthesis column A caused the urea synthesis reaction to proceed further, while going up through the synthesis column. The residence time for the reaction was 25 minutes. In the interior of the synthesis column A, baffle plates were arranged to accelerate the dispersion of gas and prevent the back mixing of liquid.

The synthesis solution fed to the stripper C through a line 4 from the top of the synthesis column A was heated in the stripper so that the ammonium carbamate was decomposed and separated as a mixed gas of ammonia and carbon dioxide. The stripper C was operated at a top temperature of 191° C., a bottom temperature of 179° C., and a top pressure of 177 bar. As described above, the apparatus was operated by circulating the gas and liquids through the condenser B, synthesis column A and stripper C. The pressure difference, serving as the driving force for this purpose, between the suction and delivery sides of the ejector, which employed the feed liquid ammonia as the driving fluid, was about 3 bar. The operating conditions and the compositions in the condenser B, synthesis column A, and stripper C are shown in Table 2.

EXAMPLE 4

A urea synthesis process shown in FIG. 4 was put in operation under the operating conditions of the condenser B, synthesis column A, and stripper C, as described in Table 2.

EXAMPLE 5

Using an apparatus with a daily production of 1,725 tons placed on the ground as shown in FIG. 3, urea synthesis was put in operation under the operating conditions of the condenser B, synthesis column A and stripper C, as described in Table 2.

TABLE 2

| | Example 3 | Example 4 | Example 5 |
|---|---|---|---|
| Feed ammonia (t/d) | 792 | 792 | 978 |
| Feed carbon dioxide (t/d) | 1025 | 1025 | 1264 |
| Recovery solution (t/d) | 1314 | 1314 | 1457 |
| Urea (%) | 0.4 | 0.4 | 0.5 |
| Ammonia (%) | 34.8 | 34.8 | 36.4 |
| Carbon dioxide (%) | 40.4 | 40.4 | 37.0 |
| Water (%) | 24.4 | 24.4 | 26.1 |
| Condenser B | | | |
| Pressure (bar) top | 175 | 175 | 156 |
| Pressure (bar) bottom | 176 | 176 | 157 |
| Temperature (° C.) | 185 | 185 | 185 |
| Urea (%) | 21.1 | 21.1 | 29.2 |
| Ammonia (%) | 34.3 | 34.3 | 32.0 |
| Carbon dioxide (%) | 26.7 | 26.7 | 18.0 |
| Water (%) | 17.9 | 17.9 | 20.8 |
| Urea synthesis rate (%) | 42.6 | 42.6 | 54 |
| N/C | 2.85 | 2.85 | 3.18 |
| H/C | 0.67 | 0.67 | 0.74 |
| Residence time (minute) | 15 | 15 | 20 |
| Volume ratio | 0.34 | 0.34 | — |
| Ejector | | | |
| Pressure (bar) suction side | 176 | 176 | 157 |
| Pressure (bar) delivery side | 179 | 179 | 160 |
| Synthesis column A | | | |
| Pressure (bar) top | 177 | 177 | 158 |
| Temperature (° C.) | 185 | 185 | 188 |
| Urea (%) | 31.8 | 31.8 | 32.9 |
| Ammonia (%) | 36.8 | 36.8 | 35.3 |
| Carbon dioxide (%) | 12.2 | 12.2 | 12.6 |
| Water (%) | 19.2 | 19.2 | 19.2 |
| Urea synthesis rate (%) | 65.7 | 65.7 | 65.5 |
| N/C | 4.0 | 4.0 | 3.8 |
| H/C | 0.67 | 0.67 | 0.62 |
| Residence time (minute) | 25 | 25 | 20 |
| Volume ratio | 0.54 | 0.54 | — |
| Stripper C (line 12) | | | |
| Pressure (bar) top | 177 | 177 | 158 |
| Urea (%) | 48.1 | 48.1 | 49.0 |
| Ammonia (%) | 13.2 | 13.2 | 13.5 |
| Carbon dioxide (%) | 13.7 | 13.7 | 12.3 |
| Water (%) | 25.0 | 25.0 | 25.2 |
| Stripper C (line 2) | | | |
| Carbon dioxide (t/d) | 969 | 969 | 863 |

EFFECTS OF THE INVENTION

According to the improved urea synthesis process of the present invention, the following effects can be achieved.

(1) Since a process, in which a synthesis column, condenser and stripper are placed on the ground, could have been established, concrete and steel-framed structures, which have hitherto been needed, are unnecessary.

(2) Where a vertical condenser is integrated with the synthesis column, simplification of the process is promoted.

(3) Since an ejector using feed liquid ammonia as the driving fluid is employed to supply the condensate to the urea synthesis column, the degree of freedom is increased in the installing location and pressure distribution of the stripper and condenser.

(4) Since the condenser is a vertical condenser, in which the feed gases and the like are fully absorbed to easily form ammonium carbamate, and employs such a structure that liquid is caused to flow through the shellside, urea is formed in the condenser by regulating the volume of the condenser.

(5) Where the urea synthesis column and the condenser are integrated, urea can be synthesized in both the condenser and the synthesis column, and therefore the total volume of these apparatuses may be made smaller than the total volume of the conventional synthesis column and condenser.

What is claimed is:

1. A urea synthesis apparatus comprising (a) a vertical urea synthesis column, (b) a vertical condenser with a cooler integrated with and above said vertical urea synthesis column, a partition wall provided between a lower urea synthesis zone functioning as a urea synthesis column and an upper condensation zone functioning as a condenser to divide them from each other, (c) a stripper for stripping unreacted ammonia and unreacted carbon dioxide, contained in a urea synthesis solution from said urea synthesis column, by means of feed carbon dioxide to separate them from the solution as a mixed gas of ammonia, carbon dioxide and water, (d) a first down pipe passing through said partition wall and located within said synthesis column and said condenser that has an opening in each of the top part of said condenser and the bottom part of said urea synthesis column and is for making said condenser communicate with said urea synthesis column to allow the condensate to flow down from the top part of said condenser to the bottom part of said urea synthesis column by gravity, (e) a piping for introducing feed ammonia or feed carbon dioxide into the bottom part of said urea synthesis column, (f) a second down pipe that has an opening in the top part of said urea synthesis column and is for introducing the urea synthesis solution into the top part of said stripper by gravity, (g) a piping for introducing said mixed gas from said stripper into the bottom part of said condenser, (h) a piping for introducing an absorption medium or an absorption medium and feed ammonia into the bottom part of said condenser, (i) a piping for discharging inert gas, joined to the top part of said condenser, (j) a piping for introducing at least a part of feed carbon dioxide, joined to the bottom part of said stripper, and (k) a piping for discharging an aqueous urea solution containing unseparated unreacted ammonia and unreacted carbon dioxide from the bottom part of said stripper for further treatments.

2. The urea synthesis apparatus according to claim 1 wherein said condenser or said synthesis column has baffle plates in the inside thereof to make gas-liquid contact better.

3. The urea synthesis apparatus according to claim 1 wherein the relative positional relations of said urea synthetic column, said condenser, and said stripper are such that when the height upto the top of said condenser from the ground level is assumed to be 100%, the height upto the bottom of said condenser is 50–80%, the height upto the top of said stripper being 20–50%, the height upto the bottom of said synthesis column being 5–30%, the height upto the bottom of said stripper being 3–10%, and the difference in height between the bottom of said condenser and the top of said stripper is 10–60%.

4. A urea synthesis apparatus comprising (a) a vertical urea synthesis column, (b) a vertical condenser with a cooler integrated with and above said vertical urea synthesis column, a partition wall provided between a lower urea synthesis zone functioning as a urea synthesis column and an upper condensation zone functioning as a condenser to divide them from each other, (c) a stripper for stripping unreacted ammonia and unreacted carbon dioxide, contained in a urea synthesis solution from said urea synthesis column, by means of feed carbon dioxide to separate them from the solution as a mixed gas of ammonia, carbon dioxide and water, (d) a heat-exchanger for preheating feed liquid ammonia, (e) an ejector using the preheated feed liquid ammonia as the driving fluid, (f) a first down pipe passing through said partition wall and located within said synthesis column and said condenser that has an opening in the top part of said condenser and is for supplying a condensate from the top part of said condenser to the suction side of the ejector, (g) a piping for introducing the feed liquid ammonia and said condensate from the delivery side of the ejector into the bottom part of said urea synthesis column, (h) a second down pipe that has an opening in the top part of said urea synthesis column and is for introducing the urea synthesis solution into the top part of said stripper, (i) a piping for introducing said mixed gas from said stripper into the bottom part of said condenser, (j) a piping for introducing an absorption medium or an absorption medium and feed ammonia into the bottom part of said condenser, (k) a piping for discharging inert gas, joined to the top part of said condenser, (l) a piping for introducing at least a part of feed carbon dioxide, joined to the bottom part of said stripper, and (m) a piping for discharging an aqueous urea solution containing unseparated unreacted ammonia and unreacted carbon dioxide from the bottom part of said stripper for further treatments.

5. The urea synthesis apparatus according to claim 4 wherein said condenser or said synthesis column has baffle plates in the inside thereof to make gas-liquid contact better.

6. The urea synthesis apparatus according to claim 4 wherein the relative positional relations of said urea synthetic column, said condenser, and said stripper are such that when the height upto the top of said condenser from the ground level is assumed to be 100%, the height upto the bottom of said condenser is 50–80%, the height upto the top of said stripper being 20–50%, the height upto the bottom of said synthesis column being 5–30%, the height upto the bottom of said stripper being 3–10%, and the difference in height between the bottom of said condenser and the top of said stripper is 10–60%.

* * * * *